United States Patent
Dalko

(10) Patent No.: US 10,682,301 B2
(45) Date of Patent: Jun. 16, 2020

(54) USE OF 4-(3-ETHOXY-4-HYDROXYPHENYL) ALKYLKETONE AS A SKIN-SOOTHING AGENT

(71) Applicant: L'OREAL, Paris (FR)

(72) Inventor: Maria Dalko, Versailles (FR)

(73) Assignee: L'OREAL, Paris (FR)

( * ) Notice: Subject to any disclaimer, the term of this patent is extended or adjusted under 35 U.S.C. 154(b) by 4 days.

(21) Appl. No.: 15/322,535

(22) PCT Filed: Jun. 30, 2015

(86) PCT No.: PCT/EP2015/064779
§ 371 (c)(1),
(2) Date: Dec. 28, 2016

(87) PCT Pub. No.: WO2016/001189
PCT Pub. Date: Jan. 7, 2016

(65) Prior Publication Data
US 2017/0231883 A1    Aug. 17, 2017

(30) Foreign Application Priority Data

Jun. 30, 2014   (FR) ...................................... 14 56176

(51) Int. Cl.
*A61K 8/35*   (2006.01)
*A61Q 19/00*  (2006.01)

(52) U.S. Cl.
CPC ................ *A61K 8/35* (2013.01); *A61Q 19/00* (2013.01); *A61Q 19/002* (2013.01)

(58) Field of Classification Search
None
See application file for complete search history.

(56) References Cited

U.S. PATENT DOCUMENTS 9,029,422 B2 * 5/2015 Dalko .................. A61Q 19/008
514/675
2012/0258058 A1  10/2012 Herrmann et al.
2012/0263768 A1 * 10/2012 Marion .................... A61K 8/35
424/401

FOREIGN PATENT DOCUMENTS

WO  WO-2011/039445 A1   4/2011
WO  WO-2012/045809 A1   4/2012
WO  WO2012131272    * 10/2012

OTHER PUBLICATIONS

Dixon et al., Ultraviolet radiation from welding and possible risk of skin and ocular malignancy. The Medical Journal of Australia, 2004, 181, 155-157.*

* cited by examiner

*Primary Examiner* — Samantha L Shterengarts
(74) *Attorney, Agent, or Firm* — Polsinelli PC

(57) ABSTRACT

The present invention relates to the non-therapeutic cosmetic use of derivatives of 4-(3-ethoxy-4-hydroxyphenyl) alkyl ketone of formula (I)

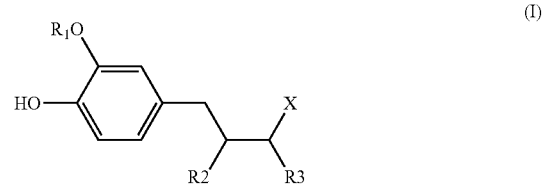

in which:
R1 represents a C1-C4 alkyl radical;
R2 represents a hydrogen atom, or a saturated or unsaturated, linear or branched C1-C6 hydrocarbon-based radical;
R3 represents a saturated or unsaturated, linear or branched C1-C4 hydrocarbon-based radical optionally substituted by a hydroxyl group;
C—X represents C=O or CH—OH;
as agent for soothing the skin of the face and/or body.

20 Claims, No Drawings

USE OF 4-(3-ETHOXY-4-HYDROXYPHENYL)ALKYLKETONE AS A SKIN-SOOTHING AGENT

CROSS REFERENCE TO RELATED APPLICATIONS

This application is a National Phase filing under 35 U.S.C. § 371 of PCT/EP2015/064779 filed on Jun. 30, 2015; and this application claims priority to Application No. 1456176 filed in France on Jun. 30, 2014 under 35 U.S.C. § 119.

The present invention relates to the non-therapeutic cosmetic use of compounds of 4-(3-ethoxy-4-hydroxyphenyl) alkyl ketone type as agents for soothing the skin of the face and the body.

The skin is the primary barrier for protecting the body from the environment. It is thus subjected to numerous external attacks which may lead to uncomfortable skin reactions. The uncomfortable skin reactions of the skin of the face or the body may especially be caused by contact with chemical products such as cleansers, permanent waves or hair dyeing, or may originate from mechanical actions such as shaving, exfoliation, scrubs or hair removal, or originate from the action of temperature, climate, or else atmospheric pollution.

There is therefore a need for novel soothing agents in the cosmetics field for the skin of the face and body.

Application WO2012/131274 describes that compounds of 4-(3-ethoxy-4-hydroxyphenyl)alkyl ketone type make it possible to eliminate and/or reduce the number of yeasts of the *Malassezia* genus, the number of dandruff flakes, and also the itching and redness on the scalp.

However, the skin of the face or body is not subjected to the same irritation of the scalp caused by the presence of a large amount of yeast of the *Malassezia* genus.

Surprisingly, the inventor has shown that the compounds of formula (I) described below have soothing properties for the skin of the face and/or body.

The present invention relates to the non-therapeutic cosmetic use, as agent for soothing the skin of the face and/or body, of a compound of formula (I) below:

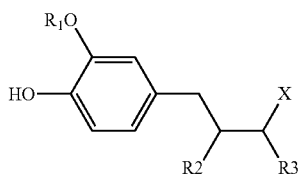

(I)

in which:
R1 represents a C1-C4 alkyl radical;
R2 represents a hydrogen atom, or a saturated or unsaturated, linear or branched C1-C6 hydrocarbon-based radical;
R3 represents a saturated or unsaturated, linear or branched C1-C4 hydrocarbon-based radical optionally substituted by a hydroxyl group;
C—X represents C=O or CH—OH.
Preferably:
R1 represents an ethyl alkyl radical;
R2 represents a hydrogen atom;
R3 represents a saturated or unsaturated, linear or branched C1-C4 hydrocarbon-based radical optionally substituted by a hydroxyl group;
C—X represents C=O or CH—OH, and preferably C=O.
Preferentially:
R1 represents an ethyl alkyl radical;
R2 represents a hydrogen atom;
R3 represents a saturated linear C1-C3 hydrocarbon-based radical;
C—X represents C=O.

As examples of compounds (I), mention may be made of:

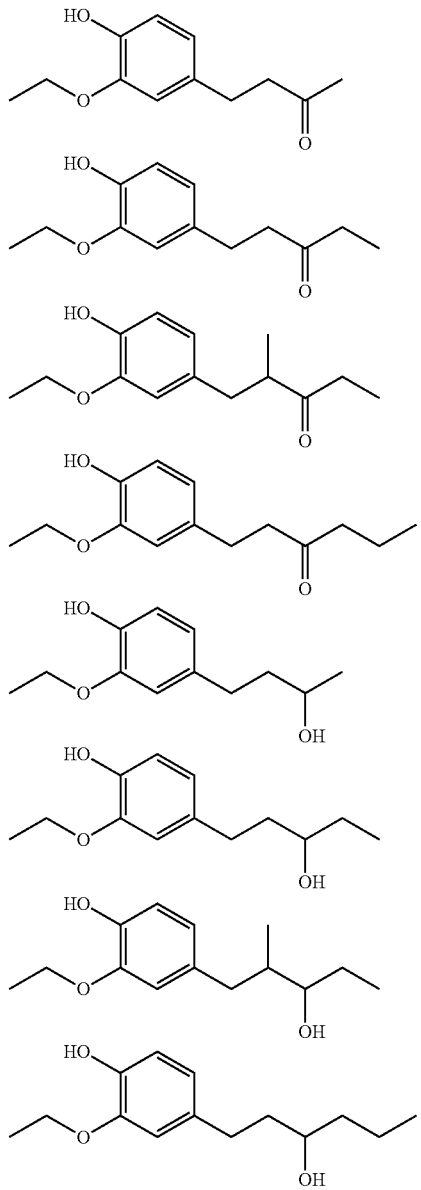

The following compound is preferably used:

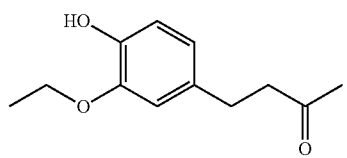

The compounds of formula (I) mentioned above may therefore be used in cosmetic compositions.

The term "cosmetic composition" means a substance or a preparation intended to be brought into contact with the various superficial parts of the human body, in particular the epidermis, the nails and the lips, with a view, exclusively or mainly, to cleansing them, fragrancing them, modifying their appearance, protecting them, keeping them in good condition, or correcting body odors. A cosmetic composition is intended for a non-therapeutic use.

The cosmetic composition is intended to be applied to the skin.

"Skin" means the skin of the face and/or the body (neck, hands, feet, legs, bust).

The cosmetic use of the compounds of formula (I) mentioned above according to the invention may be intended for preventing and/or treating unattractive reactions and/or skin discomfort, these reactions being non-pathological and possibly being caused, for example, by shaving or hair removal.

In particular, the cosmetic use according to the invention may be intended for preventing and/or treating at least one skin reaction, this reaction being non-pathological, chosen from the group consisting of redness, stinging or tautness sensations.

Generally, the non-pathological skin reactions mentioned above are most frequent in the most exposed areas of the body, namely the hands, feet, legs, face and neck. They may occur especially on areas subjected to certain daily or frequently repeated hygiene actions such as shaving (beard, legs), hair removal, cleaning with toiletry products or household products, the application of adhesives such as dressings, patches, or the attachment of prostheses, or in the case of sporting or professional actions, or simply actions associated with the way of life, with the use of clothing, tools or equipment that give rise to localized friction, or with the exposure to irritating or polluting agents or to climatic conditions.

The cosmetic compositions comprising compounds of formula (I) as defined above also comprise a physiologically acceptable medium. A physiologically acceptable medium is a non-toxic medium that may be applied to human skin and skin appendages and that has a pleasant appearance, odor and feel.

The soothing compound of formula (I) as defined above is preferably present in the cosmetic compositions in an amount of from 0.01% to 10% by weight relative to the total weight of the composition.

The soothing compound of formula (I) as defined above is preferentially present in an amount of from 0.1% to 5% by weight relative to the total weight of the composition.

The soothing compound of formula (I) as defined above is even more preferentially still present in an amount of from 0.1% to 3% by weight relative to the total weight of the composition.

The cosmetic composition may also comprise, as excipitent, at least one hydrophilic or lipophilic gelling agent, a hydrophilic or lipophilic additive, an emulsifier, a stabilizer, a preservative, a filler, a fragrance, an odor absorber, an oil, a wax, a solvent or a colorant.

The amounts of these various excipients are those conventionally used in the cosmetics field, and vary, for example, from approximately 0.01% to 15% of the total weight of the composition.

According to a particular mode of the present invention, the cosmetic composition is intended for topical administration.

For topical application to the skin, the composition may especially be in the form of aqueous or oily solutions or of dispersions of the lotion or serum type, of emulsions of liquid or semi-liquid consistency of the milk type, obtained by dispersion of a fatty phase in an aqueous phase (O/W), or vice versa (W/O), or of suspensions or emulsions of soft consistency, of the aqueous or anhydrous gel or cream type, or else of microcapsules or microparticles, or of vesicular dispersions of ionic and/or nonionic type, or of foams, preferably in the form of an emulsion. These compositions are prepared according to the usual methods.

These cosmetic or dermatological compositions may for example constitute cleansing, protective, treating or care creams for the face, the hands, the feet, the major anatomical folds or the body (for example day creams, night creams, makeup-removing creams, foundation creams or anti-sun creams), fluid foundations, makeup-removing milks, protective or care body milks, anti-sun milks, skincare lotions, gels or foams, for instance cleansing lotions, anti-sun lotions, artificial tanning lotions, bath compositions, deodorant compositions comprising a bactericidal agent, aftershave gels or lotions, and hair-removing creams.

The compositions may also consist of solid preparations constituting soaps or cleansing bars.

The compositions may also be packaged in the form of an aerosol composition also comprising a pressurized propellant.

The composition may be formulated in the form of an emulsion, cream, ointment, balm, milk, lotion, gel, foam or solution.

The cosmetic composition may in particular be chosen from shaving products, aftersun products, deodorants, soothing creams, or products specifically intended for the lips, eyes or legs.

In particular, the cosmetic composition may be chosen from aftershave balms, deodorants or soothing creams.

Another subject of the invention is a non-therapeutic cosmetic care process for soothing the skin of the face and/or body, characterized in that it comprises the application, to the skin of the face and/or body, of a cosmetic composition as described above. The process is carried out on the skin of the face and/or the body, excluding the scalp.

The cosmetic process according to the invention is intended to soothe the skin, in particular for preventing and/or reducing reactions of discomfort of the skin of the face and/or the body.

More particularly, the cosmetic process according to the invention is intended for preventing and/or treating at least one skin reaction chosen from the group consisting of redness, stinging or tautness sensations. It is in particular stinging or tautness sensations due to skin dryness.

The properties of the soothing compounds of formula (I) as defined above have been demonstrated especially by virtue of the example below.

EXAMPLE 1

A cosmetic gel having the following composition was prepared:

| | |
|---|---|
| compound (structure shown) | 0.1% |
| crosslinked acrylic acid (Carbopol 941) | 0.3% |
| water | q.s. 100% |

The gel applied to the skin of a face shaved beforehand or legs with the hair removed beforehand makes it possible to soothe the skin following shaving or hair removal.

EXAMPLE 2

The soothing properties of the compound were evaluated:

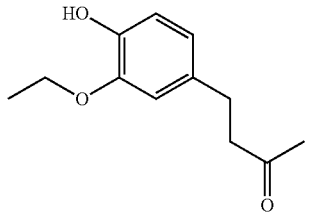

with the following protocol:
The following composition (composition A) was prepared:

| Compound | 1.6 g |
|---|---|
| 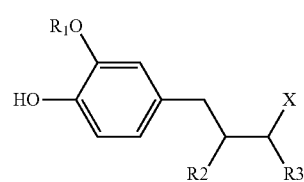 | |
| AMPS homopolymer | 0.19 g |
| Cyclohexasiloxane | 5 g |
| Dimethicone 10 cst | 3.75 g |
| Hydrogenated polyisobutylene (Parleam from NOF Corporation) | 4 g |
| Sodium hydroxide | 0.12 g |
| Propane-1,3-diol | 5 g |
| Carboxyvinyl polymer (Carbopol 980 polymer from Lubrizol) | 0.3 g |
| Acrylic acid/$C_{10}$-$C_{30}$ alkyl methacrylate crosslinked copolymer (Pemulen TR-2 Polymer from Lubrizol) | 0.11 g |
| Neutralized polyacrylamidomethylpropanesulfonic acid partially neutralized with ammonia and highly crosslinked (Hostacerin AMPS ® from Clariant) | 0.2 |
| Citric acid | 0.08 g |
| Water q.s. | 100 g |

A placebo composition (composition P) was also prepared, without the ketone composition, replacing the amount thereof with water.

A test panel with 10 men was conducted to evaluate composition A and with 9 men to evaluate composition P. The men on the panels have white skin.

Each subject applied the composition after shaving in the morning and also in the evening before going to bed, for 5 days.

A first evaluation or measurement was carried out on the first day 20 minutes after shaving, then a second evaluation or measurement was made on the 5th day 20 minutes after shaving, as described below.

Measurement of Skin Redness:
Skin redness was measured with a chromameter (Konica Minolta CR-400, D65 Daylight mode) on the area of the face treated with the composition and the untreated area. The color was measured using the CIE L a b system and the value was graded (3 measurements carried out).

With composition A, a reduction in the redness of 4.1% was obtained, while with the placebo composition the reduction in redness is 1.4%.

Evaluation of the Tautness Sensation of Skin Dryness:
The panel was also asked to evaluate the tautness sensation of skin dryness on the first day and on the fifth day of treatment, according to the following rating:
0=none
1=mild
2=moderate
3=severe The mean grade awarded by the panel on the first and fifth day of treatment was then calculated, then the percentage difference was determined between the The following results were obtained:
Composition A:
Mean first day=0.90
Mean fifth day=0.30
i.e. a difference of 0.3/0.9×100=33.3%
Composition P:
Mean first day=0.78
Mean fifth day=0.44
i.e. a difference of 0.44/0.78×100=57.1%

The panel treated with composition A perceives a milder tautness sensation of skin dryness than that perceived by the panel treated with composition P.

The results obtained show that the ketone composition tested makes it possible to reduce skin redness and also the tautness sensation of skin dryness caused by shaving. The ketone composition therefore has a skin soothing action after shaving.

The invention claimed is:

1. A non-therapeutic cosmetic process for soothing facial and/or body skin by preventing and/or treating at least one non-pathological skin reaction selected from the group of redness, stinging or tautness sensations caused by at least one action selected from the group of frequently repeated hygiene action, cleaning with toiletry or household products, applying adhesives to the skin, localized skin friction, or exposure to polluting agents, comprising topically applying to the skin an effective amount for soothing the skin of a compound of formula (I) below:

(I)

$R_1O$
HO— —X
    $R_2$ $R_3$ in which:
$R_1$ represents a C1-C4 alkyl radical;
R2 represents a hydrogen atom, or a saturated or unsaturated, linear or branched C1-C6 hydrocarbon-based radical;
R3 represents a saturated or unsaturated, linear or branched C1-C4 hydrocarbon-based radical optionally substituted by a hydroxyl group; and
C—X represents C=O or CH—OH.

2. The process as claimed in claim 1, which comprises applying to the skin a cosmetic composition containing the compound of formula (I) below to the skin

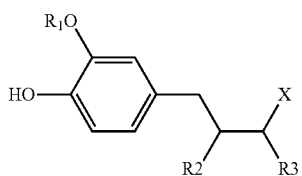
(I)

in which:
R₁ represents a C1-C4 alkyl radical;
R2 represents a hydrogen atom, or a saturated or unsaturated, linear or branched C1-C6 hydrocarbon-based radical;
R3 represents a saturated or unsaturated, linear or branched C1-C4 hydrocarbon-based radical optionally substituted by a hydroxyl group; and
C—X represents C=O or CH—OH.

3. The process as claimed in claim 1, wherein the compound of formula (I) is present in a cosmetic composition in an amount ranging from 0.01% to 10% by weight relative to the total weight of the composition.

4. The process as claimed in claim 1, in which, for the compound of formula (I):
R₁ represents an ethyl alkyl radical;
R2 represents a hydrogen atom;
R3 represents a saturated or unsaturated, linear or branched C1-C4 hydrocarbon-based radical optionally substituted by a hydroxyl group; and
C—X represents C=O or CH—OH.

5. The process as claimed in claim 1, in which, for the compound of formula (I):
R₁ represents an ethyl alkyl radical;
R2 represents a hydrogen atom;
R3 represents a saturated linear C1-C3 hydrocarbon-based radical; and
C—X represents C=O.

6. The process as claimed in claim 1, in which the compound of formula (I) is chosen from:

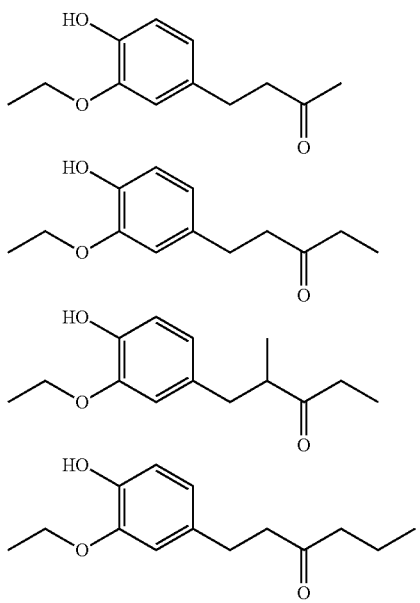

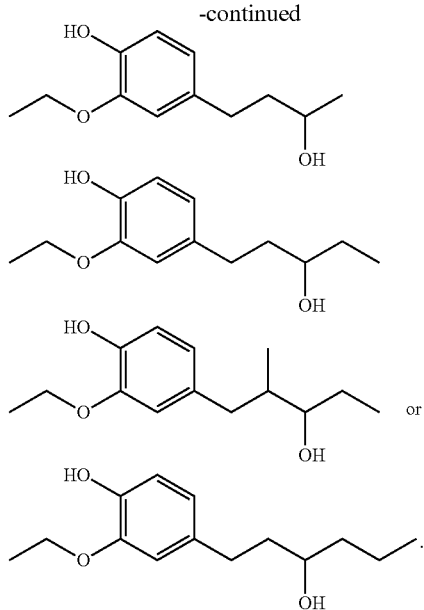

7. The process as claimed in claim 1, in which the compound of formula (I) is:

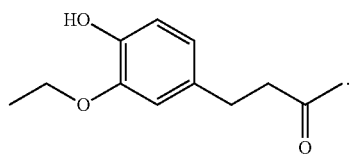

8. The process as claimed in claim 1, wherein the compound of formula (I) is present in a cosmetic composition in an amount ranging from 0.1% to 5% by weight relative to the total weight of the composition.

9. The process as claimed in claim 2, in which, for the compound of formula (I):
R₁ represents an ethyl alkyl radical;
R2 represents a hydrogen atom;
R3 represents a saturated or unsaturated, linear or branched C1-C4 hydrocarbon-based radical optionally substituted by a hydroxyl group; and
C—X represents C=O or CH—OH.

10. The process as claimed in claim 2, in which, for the compound of formula (I):
R₁ represents an ethyl alkyl radical;
R2 represents a hydrogen atom;
R3 represents a saturated linear C1-C3 hydrocarbon-based radical; and
C—X represents C=O.

11. The process as claimed in claim 2, in which the compound of formula (I) is chosen from:

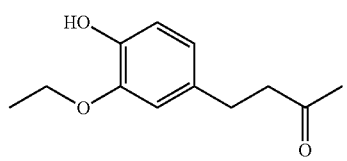

-continued

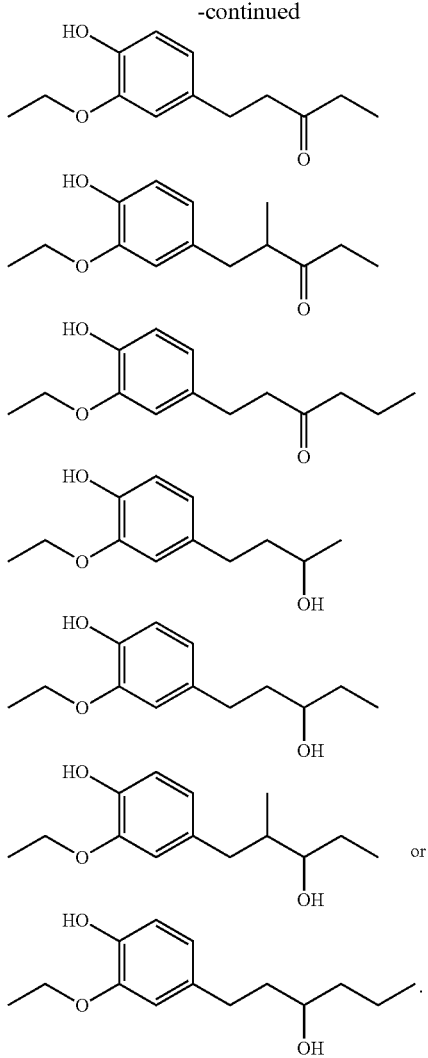

12. The process as claimed in claim 2, in which the compound (I) is:

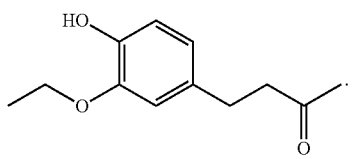

13. The process as claimed in claim 2, wherein the compound of formula (I) is present in a cosmetic composition in an amount ranging from 0.1% to 5% by weight relative to the total weight of the composition.

14. The process as claimed in claim 3, in which, for the compound of formula (I):
R₁ represents an ethyl alkyl radical;
R2 represents a hydrogen atom;
R3 represents a saturated or unsaturated, linear or branched C1-C4 hydrocarbon-based radical optionally substituted by a hydroxyl group; and
C—X represents C=O or CH—OH.

15. The process as claimed in claim 3, in which, for the compound of formula (I):
R₁ represents an ethyl alkyl radical;
R2 represents a hydrogen atom;
R3 represents a saturated linear C1-C3 hydrocarbon-based radical; and
C—X represents C=O.

16. The process as claimed in claim 3, in which the compound of formula (I) is chosen from:

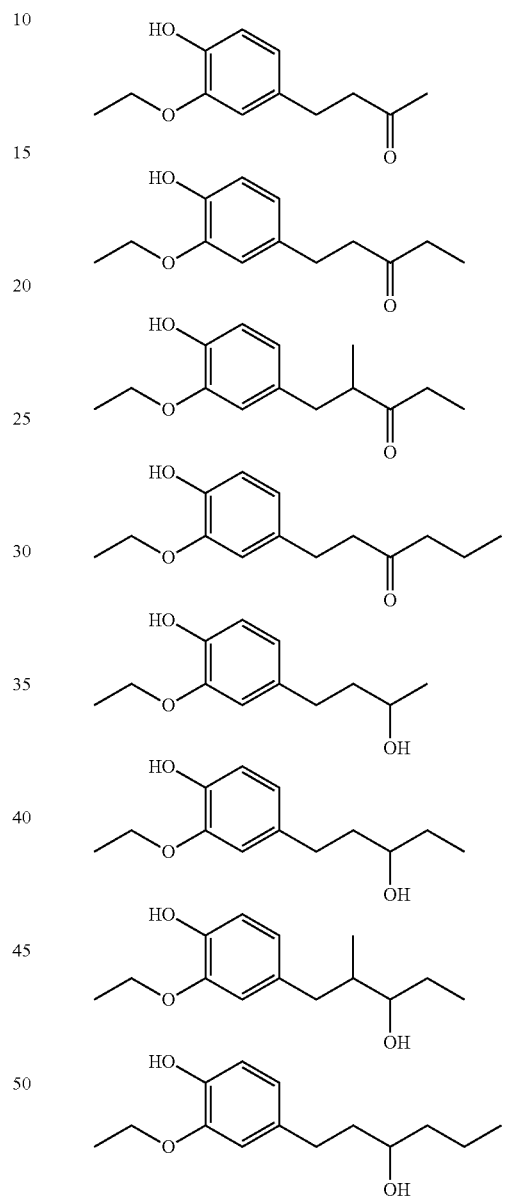

17. The process as claimed in claim 3, in which the compound of formula (I) is:

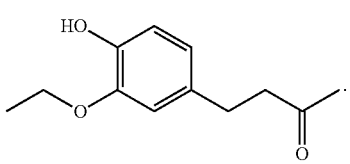

18. The process as claimed in claim 17, wherein the compound of formula (I) is present in a cosmetic composition in an amount ranging from 0.1% to 5% by weight relative to the total weight of the composition.

19. The process as claimed in claim 1 wherein the at least one non-pathological skin reaction is caused by at least one action selected from the group of frequently repeated hygiene action, cleaning with toiletry or household products, applying adhesives to the skin, and localized skin friction.

20. The process as claimed in claim 1 wherein the at least one non-pathological skin reaction is caused by shaving.

* * * * *